US009205203B2

(12) United States Patent
Dogwiler et al.

(10) Patent No.: US 9,205,203 B2
(45) Date of Patent: Dec. 8, 2015

(54) LIQUID DRUG DEGASSING DEVICE AND AMBULATORY INFUSION SYSTEM INCLUDING A DEGASSING DEVICE

(71) Applicant: Roche Diagnostics International AG, Rotkreuz (CH)

(72) Inventors: Joerg Dogwiler, Bergdietikon (CH); Christoph Huwiler, Arth (CH); Philipp Michel, Kirchlindach (CH)

(73) Assignee: Roche Diagnostics International AG, Rotkreuz (CH)

( * ) Notice: Subject to any disclaimer, the term of this patent is extended or adjusted under 35 U.S.C. 154(b) by 384 days.

(21) Appl. No.: 13/630,091

(22) Filed: Sep. 28, 2012

(65) Prior Publication Data

US 2013/0267896 A1 Oct. 10, 2013

Related U.S. Application Data

(63) Continuation of application No. PCT/EP2011/001522, filed on Mar. 25, 2011.

(30) Foreign Application Priority Data

Mar. 31, 2010 (EP) .................................... 10003572
Sep. 16, 2010 (EP) .................................... 10009698

(51) Int. Cl.
*A61M 5/38* (2006.01)
*B01D 19/00* (2006.01)

(Continued)

(52) U.S. Cl.
CPC ........... *A61M 5/385* (2013.01); *A61M 5/14244* (2013.01); *A61M 5/36* (2013.01);

(Continued)

(58) Field of Classification Search
CPC ........... A61B 17/3462; A61B 17/3498; A61B 17/3421; A61B 17/3474; A61M 39/06; A61M 5/38; A61M 5/385; B01D 19/0031
USPC ....................................... 604/167.03–167.06
See application file for complete search history.

(56) References Cited

U.S. PATENT DOCUMENTS 6,347,711 B1 * 2/2002 Goebel et al. ................ 210/436
7,238,224 B2 7/2007 Kent (Continued)

FOREIGN PATENT DOCUMENTS

GB 1401382 A 7/1975
GB 2000685 A 1/1979

(Continued)

OTHER PUBLICATIONS

International Search Report for Application No. PCT/EP2011/001522 dated Aug. 9, 2011.

(Continued)

*Primary Examiner* — Nicholas Lucchesi
*Assistant Examiner* — Anh Bui
(74) *Attorney, Agent, or Firm* — Dinsmore & Shohl LLP

(57) ABSTRACT

Embodiments directed to a degassing device for removing gas bubbles from a liquid drug stream and an ambulatory infusion system are disclosed. The degassing device may comprise an inlet chamber with an inlet opening, an outlet chamber with an outlet opening, and a degassing opening. A hydrophilic membrane and a hydrophobic membrane, wherein the hydrophilic membrane fluidically couples the inlet chamber with the outlet chamber, enabling a transfer of liquid from the inlet chamber to the outlet chamber. The hydrophobic membrane fluidically couples the inlet chamber with the degassing opening, enabling a transfer of gas from the inlet chamber to the degassing opening. The hydrophilic and hydrophobic membranes being joined along a joint to establish a joined membrane, such that a contact line of a liquid-gas phase separation on the joined membrane does not coincide with the joint independent of an orientation of the degassing device with respect to gravity.

15 Claims, 9 Drawing Sheets

104 100 110a 120 110 112a 108 112 116 110b 124 114 122 106

(51) Int. Cl.

*A61M 5/142* (2006.01)
*A61M 5/36* (2006.01)
*B01D 53/22* (2006.01)
*B01D 63/08* (2006.01)

(52) U.S. Cl.

CPC ................ *A61M 5/38* (2013.01); *B01D 19/00* (2013.01); *B01D 19/0031* (2013.01); *B01D 53/22* (2013.01); *B01D 63/08* (2013.01); *A61M 2205/75* (2013.01); *A61M 2205/7527* (2013.01); *A61M 2205/7536* (2013.01); *B01D 2313/365* (2013.01); *B01D 2313/90* (2013.01); *B01D 2325/36* (2013.01); *B01D 2325/38* (2013.01)

(56) References Cited

U.S. PATENT DOCUMENTS

2003/0130625 A1* 7/2003 Jacobson et al. ............. 604/253
2007/0083153 A1 4/2007 Haar
2008/0051710 A1 2/2008 Moberg et al.

FOREIGN PATENT DOCUMENTS

| | | | |
|---|---|---|---|
| WO | 0025844 | A1 | 5/2000 |
| WO | 0243841 | A2 | 6/2002 |
| WO | 03053498 | A2 | 7/2003 |
| WO | 2005105182 | A1 | 11/2005 |
| WO | 2005115595 | A1 | 12/2005 |
| WO | 2007131567 | A1 | 11/2007 |
| WO | 2008110263 | A1 | 9/2008 |

OTHER PUBLICATIONS

European Search Report for Application No. EP 10 00 9698 dated Jan. 12, 2012.

* cited by examiner

LIQUID DRUG DEGASSING DEVICE AND AMBULATORY INFUSION SYSTEM INCLUDING A DEGASSING DEVICE

CROSS-REFERENCE TO RELATED APPLICATIONS

This application is a continuation of International application PCT/EP2011/001522, filed Mar. 25, 2011, which claims priority to EP application 10003572.4, filed Mar. 31, 2010 and EP application 10009698.1, filed Sep. 16, 2010.

TECHNICAL FIELD

The present disclosure is related to a degassing device for liquid drugs, and to an ambulatory infusion system comprising a degassing device.

BACKGROUND

Ambulatory infusion systems are known in the art for a variety of applications. In particular, ambulatory infusion systems adapted for insulin administration form a basis for state-of-the-art therapy of diabetes mellitus by CSII (Continuous Subcutaneous Insulin Infusion). These systems are typically computer controlled micro-dosing pumps that are adapted to be worn continuously and concealed from view. The insulin is infused via a subcutaneous cannula that is replaced by a user, e.g., a PwD (Person with Diabetes) or a relative of such a person, every few days. Such insulin pumps are commercially available from a number of suppliers.

Insulin pumps are typically designed to infuse an insulin formulation or another liquid drug continuously according to a basal administration profile that is variable over the time of day. In addition, infusion pumps are often designed to infuse larger drug boli in a comparatively short time interval on demand. In CSII, insulin boli are typically administered to compensate food intake and to lower an undesirably raised blood glucose level. The total daily amount of infused insulin may vary depending on personal factors and habits of a PwD in a considerable range (between, e.g., 10 IU to 80 IU, with 100 IU (International units) corresponding to 1 ml of a liquid insulin formulation for the currently most common concentration of liquid insulin formulations).

CSII therapy may be used in the field of application. Phrases like “infusion system” or “infusion device” may therefore refer to systems and devices which are suitable for CSII and similar applications, such as various hormone therapies, pain therapy or cancer treatment.

Infusion systems may include a positive-displacement pump of the syringe-driver type coupled to a cylindrical drug cartridge out of which a liquid drug formulation is forced into an infusion line by displacing a cartridge plunger in a controlled manner. Reference is made to WO 2003053498 A2 and WO 2000025844 A1 regarding the design and features of a state-of-the-art infusion pump. However, the present disclosure is not limited to a specific therapy or system design.

While complete filling of the drug containers is generally desirable, some air typically remains in a drug container and is subsequently infused into the body along with the liquid drug. This holds especially true if the drug cartridge is not filled by a trained and experienced professional and under well-controlled conditions, but is filled by a user at home as it is typically the case in CSII therapy. In addition, some air is typically dissolved in a liquid insulin formulation which outgases during application, thus forming air bubbles. The infusion of air, however, is generally undesired. Furthermore, it is disadvantageous if a pressure sensor is used in the system for detecting blockages and/or occlusions as will be discussed below in more detail, wherein it may be desirable to remove the air from the drug stream prior to infusion into the body.

U.S. Pat. No. 7,238,224 discloses a degassing device that may be used for removing gas, e.g., air, from a liquid. The device includes a chamber with an inlet as well as a hydrophilic membrane and a hydrophobic membrane which are arranged at opposing walls of the chamber. If a mixture of liquid and gas, e.g., a liquid stream with air bubbles, is supplied via the inlet, the liquid passes through the hydrophilic membrane to an outlet while the gas passes through the hydrophobic membrane, which is in contact with the environment. Operation of the device, however, is highly dependent on its orientation with respect to gravity as well as the relative amounts of liquid and gas inside the chamber. In dependence of these factors, the hydrophilic membrane may only be in contact with gas while the hydrophobic membrane may simultaneously only be in contact with liquid. Since the hydrophilic membrane is, once wetted, non-permeable for gas and the hydrophobic membrane is non-permeable for liquid, neither of the liquid nor the gas can exit the chamber, resulting in a blockage. Therefore, the degassing device is not suited for an ambulatory infusion system that is carried by a person night and day and that may take any spatial orientation.

U.S. Pat. No. 6,347,711 B1 discloses a filter for medical fluids with a hydrophilic membrane and two hydrophobic membranes on opposes sides of the device, wherein one of the hydrophobic membranes is in a common plane with the hydrophilic membrane.

SUMMARY

In one embodiment, a degassing device for removing gas bubbles from a liquid drug stream is disclosed. The degassing device may comprise an inlet chamber with an inlet opening, an outlet chamber with an outlet opening, and a degassing opening; and a hydrophilic membrane and a hydrophobic membrane, wherein the hydrophilic membrane fluidically couples the inlet chamber with the outlet chamber, enabling a transfer of liquid from the inlet chamber to the outlet chamber through the hydrophilic membrane, the hydrophobic membrane fluidically couples the inlet chamber with the degassing opening, enabling a transfer of gas from the inlet chamber to the degassing opening through the hydrophobic membrane, and, the hydrophilic membrane and the hydrophobic membrane being joined along a joint to establish a joined membrane, such that a contact line of a liquid-gas phase separation on the joined membrane does not coincide with the joint independent of an orientation of the degassing device with respect to gravity.

In another embodiment, an ambulatory infusion system is disclosed. The ambulatory infusion system may comprise a drug container; a cannula assembly including a subcutaneous cannula, the subcutaneous cannula being fluidically coupled to the drug container; a degassing device comprising an inlet chamber with an inlet opening, an outlet chamber with an outlet opening, and a degassing opening, wherein the inlet opening of the degassing device is fluidically coupled to the drug container and the outlet opening of the degassing device is fluidically coupled to the subcutaneous cannula, and a hydrophilic membrane and a hydrophobic membrane, wherein the hydrophilic membrane fluidically couples the inlet chamber with the outlet chamber, enabling a transfer of liquid from the inlet chamber to the outlet chamber through the hydrophilic membrane, the hydrophobic membrane fluidically couples the inlet chamber with the degassing opening, enabling a transfer of gas from the inlet chamber to the degassing opening through the hydrophobic membrane, the hydrophilic membrane and the hydrophobic membrane being joined along a joint to establish a joined membrane, such that a contact line of a liquid-gas phase separation on the joined membrane does not coincide with the joint independent of an orientation of the degassing device with respect to gravity; and a dosing unit, the dosing unit operatively coupled to the drug container.

DETAILED DESCRIPTION

Figure 1:
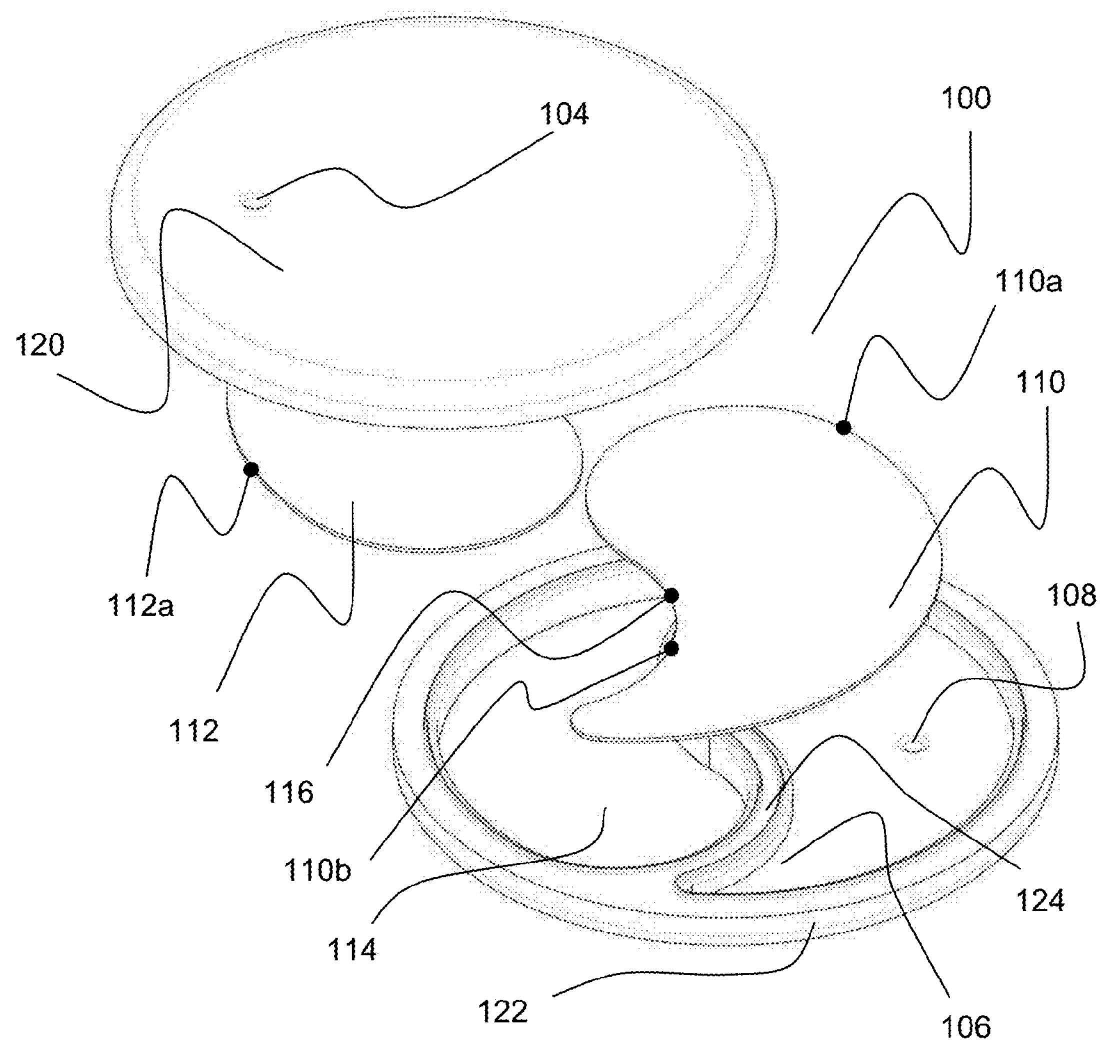
FIG. 1 shows an embodiment of a degassing device in an exploded view.

It is an objective of the present disclosure to provide a degassing device that may operate independently of its spatial orientation with respect to gravity and may be used in ambulatory infusion systems.

The objective is achieved based on the insight that orientation-dependency can be considerably reduced by arranging a hydrophilic membrane and a hydrophobic membrane such that they may form, in combination, a joined membrane with a hydrophilic section and a hydrophobic section. Thus, the device can be designed such that a liquid flow is enabled from the inlet through the hydrophilic membrane at any time independent of its orientation while gas can escape via the hydrophobic membrane. Operation of a degassing device in accordance with the present disclosure may be independent of its orientation while requiring at least one hydrophilic and hydrophobic membrane, respectively.

The term "orientation" generally refers to the spatial orientation of the device with respect to gravity where not explicitly stated differently. The term "drug" refers generally to a liquid drug formulation which may, however, also include some gas, such as air. The term "degassing" refers to the removal of gas from a drug flow.

A degassing device in accordance with an embodiment of the present disclosure may comprise an inlet chamber with an inlet opening, an outlet chamber with an outlet opening, and a degassing opening, and a hydrophilic membrane and a hydrophobic membrane.

The hydrophilic membrane fluidically couples the inlet chamber with the outlet chamber, thus enabling a transfer of liquid from the inlet chamber to the outlet chamber through the hydrophilic membrane. Similarly, the hydrophobic membrane fluidically couples the inlet chamber with the degassing opening, thus enabling a transfer of gas from the inlet chamber to the degassing opening through the hydrophobic membrane.

The hydrophilic membrane and the hydrophobic membrane are joined along a joint to establish a joined membrane.

The hydrophilic membrane and the hydrophobic membrane may directly contact each other along the joint. In dependence of the technical realization of the joint, a seam may be present along the joint. The hydrophilic and hydrophobic membranes may in some embodiments be separated along the joint via a small rim or the like. The presence of a separation such as a rim or a seam along the joint is not critical as long as the transition of the hydrophilic membrane and the hydrophobic membrane is substantially continuous. The separation, if present, should have a width that is small as compared to the lateral dimensions of the membrane. For illustrative purposes, the joint may therefore also be considered as a curve in the geometrical sense, i.e., as a one-dimensional line with no lateral extension.

The degassing device may be designed for gases and liquids having different physical properties. For example, the liquid may be an aqueous solution of low viscosity and the gas may be air.

The drug is forced into the inlet chamber of the degassing device with some over-pressure, such that a pressure-gradient is present across the hydrophilic membrane and across the hydrophobic membrane, respectively. This condition is fulfilled for a positive displacement pump, such as a syringe-driver, a peristaltic pump or a membrane pump upstream of the degassing device.

According to embodiments of the present disclosure, the degassing device is designed for a maximum liquid flow of 0.5 ml/min or less, in particular for a maximum liquid flow in the range of 0.05 ml/min to 0.4 ml/min. Such a liquid flow is a typical maximum liquid flow in ambulatory infusion devices and systems as used in CSII when filling a fresh infusion tubing (priming) and during insulin bolus delivery. In some embodiments, the degassing device is designed for a liquid flow of about 0.2 ml/min (corresponding to 20 IU (International Units) per minute of the currently most common liquid insulin formulations).

A variety of materials may be used for the hydrophilic membrane and the hydrophobic membrane. In one embodiment, the hydrophilic membrane is made of PES (Polyethersulfon) and the hydrophobic membrane is made of PTFE (Polytetrafluoroethylene). Both types of membranes are commercially available. Further membrane materials that may be used are, among others, Acrylic Copolymer, Nylon, Polyethersulfone (aPES, PES), Polyvinylidene fluride (PVDF), Acrylic Copolymer, Polysofone (MMM), Polypropylene. Suited membranes are available, among others, from PALL Life sciences, USA.

The membrane areas are selected in dependence of the drug flow per time, the involved pressure and the relative amounts of liquid and gas. In another embodiment, the areas of the hydrophilic membrane and the hydrophobic membrane are equal. If the amount of gas is expected to be high, the area of the hydrophobic membrane may be larger as compared to the area of the hydrophilic membrane. If only single and small gas bubbles are present, in contrast, the area of the hydrophobic membrane may be considerably smaller as compared to the area of the hydrophilic membrane. In the context of CSII therapy with the above-given membrane materials, the cross-sectional areas of the membranes may each be in a range of about 20 $mm^2$ to 60 $mm^2$. Suited membranes and membrane sizes can be determined by a person skilled in the art based on the corresponding membrane data sheets.

The thickness of the membranes should generally be small to keep the flow resistance low. A lower limit is determined by the production technology of the membranes, the mechanical stability with respect to bending, as well as the fluidic pressure gradients over the membranes. The thickness of the membranes may be in a range from about 50 micrometers to 1 millimeter.

Further components of the degassing device, such as a housing, may, for example, be made from injection-molded plastics or another suited material, such as stainless steel or ceramics.

In another embodiment, the joint is designed to be non-straight and non-circular. Such that small gas bubbles in the liquid stream may be spherical in the inlet chamber if the gas bubbles are small as compared to the dimensions of the inlet chamber. For a larger amount of gas, the gas bubble contacts the limiting surfaces of the chamber, resulting in a different geometry of the liquid-gas phase separation than spherical.

In another embodiment, the inlet chamber is cylindrical, with the joined membrane being one of its cover surfaces. Furthermore, its height, i.e., its axial dimension, is considerably smaller than its diameter. Consequently, the joined membrane has a circular surface and the degassing device has a disk-like shape. If the degassing device is oriented such that the cylinder axis is aligned with gravity, a gas bubble inside the inlet chamber may assume the form of a gas cylinder, with the height of the gas cylinder corresponding to the height of the inlet chamber. The circumferential contact line of the gas cylinder on the joined membrane may be circular in this case. For the joint being circular, a situation may therefore occur where the contact line coincidences with the joint, such that the hydrophilic membrane is only in contact with gas and the hydrophobic membrane is only in contact with liquid. Consequently, the degassing device is blocked in this situation since neither liquid nor gas can exit the inlet chamber. This is prevented by a non-circular geometry of the joint curve. If the degassing device is tilted with respect to gravity, the liquid-gas phase separation may take the form of a plane with the contact line of the liquid gas phase separation on the spit-membrane being a straight line. For the joint being straight, too, a situation may therefore occur where the straight contact line coincidences with the straight line of the joint such that the degassing device is blocked as described above. Thus, blockage of the degassing device may be prevented by the joint being non-straight.

In a further embodiment, the joint may be designed such that a contact line of a liquid-gas phase separation on the joined membrane is separate from the joint or crosses the joint for all orientations of the degassing device, but does not coincide with the joint. This condition should be met at any time during application of the degassing device.

In some embodiments, the joint is twofold bent. The joint may have the form of a twisted or non-twisted curve. In the case of a non-twisted, two-fold bent joint, it may have to form of an “S”.

In another embodiment, the hydrophilic membrane is planar and the hydrophobic membrane is planar. In alternative embodiments, the hydrophilic and hydrophobic membranes may have different geometries and are, for example, sections of a paraboloid or an ellipsoid of revolution or of a sphere.

In a further embodiment wherein both the hydrophilic membrane and the hydrophobic membrane each being planar, both membranes are co-planar, resulting in a planar joined membrane.

In yet a further embodiment, the joint has two end points, the two end points being on a periphery of the joined membrane. In such an embodiment, the hydrophilic membrane and the hydrophobic membrane may, for example, be arranged side-by-side in a common plane, such that the joint, for example, an “S” curved joint as described above, divides the joined membrane into a hydrophilic section and a hydrophobic section in a side-by-side arrangement. Instead of being planar, the joined membrane may also be curved. In a further embodiment, the hydrophilic membrane and the hydrophobic membrane are each planar, but the corresponding planes are angled with respect to each other and the contact line between the two planes is given by the joint.

In another embodiment, the joint is closed, that is, has the form of a closed curve. In such an embodiment, either of the hydrophilic membrane or the hydrophobic membrane may be arranged as an inner membrane in a cut-out of the other outer membrane. The joint may, for example, be elliptical or a close polygon and be triangular, rectangular, hexagonal, or the like. Alternatively, the joint has the geometry of a twisted and closed curve.

In another embodiment, a peripheral surface of the inlet chamber is parallel to a peripheral surface of the outlet chamber, the peripheral surface of the inlet chamber facing the peripheral surface of the outlet chamber. The peripheral surface of the inlet chamber and the outlet chamber, respectively, are realized by corresponding inner surfaces of housing walls of the degassing device. In such an embodiment, the degassing device may have the form of a circular or non-circular disk with inner surfaces of the cover walls being the peripheral surfaces of the inlet chamber and the outlet chamber, respectively.

In another embodiment, the joined membrane is arranged between the peripheral surfaces of the inlet chamber and the outlet chamber, respectively.

In another embodiment, the degassing device includes a support structure, the support structure supporting the joined membrane along the joint. Wherein the support structure may be a rim or wall that is integral with the degassing device housing and has a form corresponding to the joint. The support structure may further serve as wall of the outlet chamber which separates the outlet chamber and the degassing opening in a side-by-side arrangement of the outlet chamber and the degassing opening.

In another embodiment, the hydrophilic membrane and the hydrophobic membrane are permanently attached to the support structure. This may be performed by technologies such as adhesive bonding, ultrasonic welding or laser welding.

Further embodiments may include a liquid pressure sensor for measuring a liquid pressure downstream of the hydrophilic membrane. A pressure sensor may be used in an ambulatory infusion system for general infusion supervision purposes and may be used for detecting error conditions, such as an occluded infusion cannula. For a positive-displacement pump, a cannula occlusion is generally associated with a comparatively steep increase of the fluidic pressure over time, resulting from the liquid being incompressible and the stiffness of the system being high. An occlusion may therefore be detected via pressure measurements in combination with a corresponding evaluation algorithm, as disclosed, for example, in WO 2005105182 A1.

Because of the low infusion rates, the time delay for detecting an occlusion may, however, be in the range of several hours and result in severe medical complications.

If air or another gas, which is inherently highly compressible, is present in the fluidic system, the overall fluidic stiffness is considerably reduced, resulting in a smaller pressure increase over time in case of an occlusion. By removing gas from the drug upstream of the pressure sensor via a degassing device in accordance embodiments of the present disclosure, the undesired effect can be avoided and the detection delay for occlusion may be greatly reduced. As well as the time delay for detecting an occlusion may be reduced from several hours to about half an hour or less.

The pressure sensor may include a generally rigid measurement chamber with an inlet and an outlet and a pressure transfer membrane that is deflected by the fluidic pressure. The deflection is determined by means of a capacitive or optical transducer, strain gauges, or the like. Alternatively or additionally, the membrane deflection may switch the state of one or more switching contacts.

The measurement chamber may be a dedicated measurement chamber that is fluidically arranged between the outlet of the degassing device and an infusion cannula. Alternatively, a pressure transfer membrane may be incorporated into the outlet chamber of the degassing device, such that the outlet chamber additionally may serve as a measurement chamber. In another embodiment, the measurement chamber may be replaced by a flexible wall of a fluid channel between the degassing device and the infusion cannula. Further aspects of the pressure sensors are discussed below in the context of further embodiments. The pressure-sensor may further be a solid-state pressure sensor that is directly integrated into a drug channel wall of the degassing device.

A further embodiment of the present disclosure is directed towards ambulatory infusion systems. Embodiments of such an ambulatory infusion system may include a drug container, a cannula assembly including a subcutaneous cannula, the subcutaneous cannula, during application, may be fluidically coupled to the drug container, a degassing device as described above, wherein the inlet opening of the degassing device, during application, may be fluidically coupled to the drug container and the outlet opening of the degassing device, during application, may be fluidically coupled to the subcutaneous cannula, a dosing unit, wherein the dosing unit, during operation, may be operatively coupled to the drug container.

In another embodiment, the cannula assembly may be designed to be adhesively attached to a person's s skin for drug infusion over an extended time period. The subcutaneous cannula has a typical length in the range of some millimeters up to about 2 cm and may be made of medical grade stainless steel or a soft material, such as PTFE. The cannula may be used for an application time of some days and may be replaced by the user afterwards.

The ambulatory infusion system may especially be designed for use in CSII therapy or similar applications. The drug container may have a filling volume in the range of about 1 ml to 4 ml and may be replaced by a user every few days.

In another embodiment, the ambulatory infusion system may include an electronic controller. The electronic controller, during operation, may be operatively coupled to the dosing unit and designed to control the operation of the dosing unit. In the context of CSII therapy, the controller may be designed to control the dosing unit for infusion in a substantially continuous way according to a time-variable basal profile and for additionally infusing larger drug boli as described above.

In another embodiment, the degassing device may be integral with at least one of the cannula assembly or the drug container.

Further aspects and variants of an ambulatory infusion system will be discussed below.

According to a still further embodiment, the present disclosure may be directed towards a cannula assembly, the cannula assembly including a subcutaneous cannula and a degassing device according to the present disclosure in an integral unit. According to a still further embodiment, the container assembly including a drug container as discussed above for use in or in combination with an ambulatory infusion device as well as a degassing device according to embodiments of the present disclosure in an integral unit.

Further variants and embodiments and typical characteristics may be unambiguously derived by a person skilled in the art from the disclosure given with reference to degassing devices and ambulatory infusion systems.

Embodiments of the present disclosure are discussed in more detail with reference to the following Figures.

Figure 2:
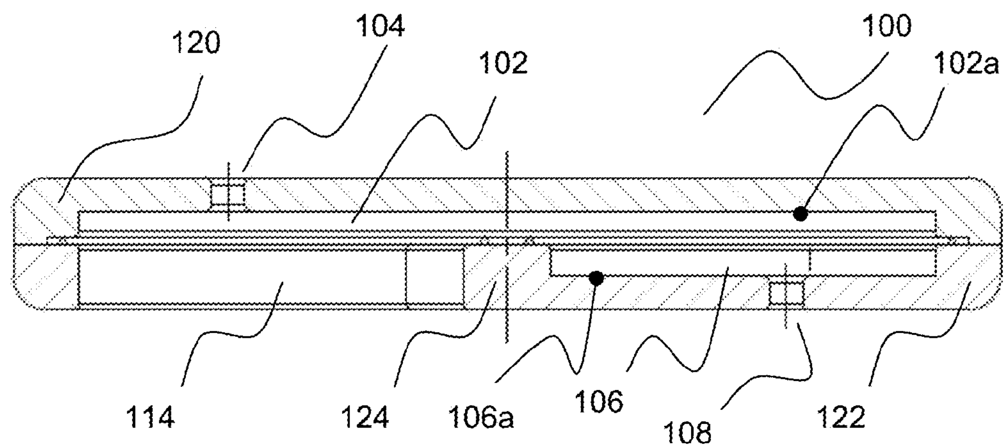
FIG. 2 shows a sectional view of the degassing device of FIG. 1.
Figure 3:
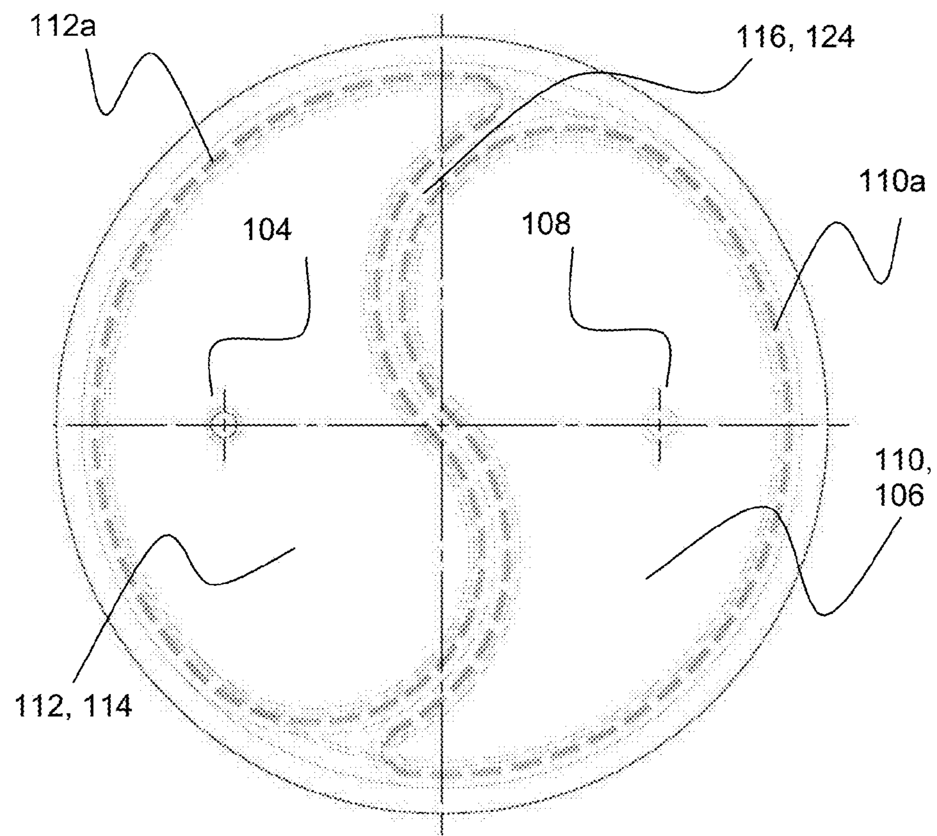
FIG. 3 shows a top view of the degassing device of FIG. 1.

FIGS. 1, 2 and 3 show a degassing device 100. FIG. 1 shows the degassing device 100 in an exploded view; FIG. 2 shows a sectional view; and FIG. 3 a top view, additionally indicating the sectional plane for FIG. 2. For clarity reasons, these figures show the degassing device 100 alone and without additional components, such as tubing or fittings that may be present.

The degassing device 100 includes a housing which is realized by an upper housing shell 120 and a lower housing shell 122, made from injection-molded plastics. In the assembled state, the housing shells 120, 122 are permanently attached to each other along their circumference at corresponding contacting edges (not referenced) by technologies such as adhesive bonding, laser welding or ultrasonic welding, resulting in an overall cylindrical disc shape of the degassing device 100. An inlet opening 104 in the upper housing shell 120 is in fluidic communication with inlet chamber 102 inside the device 100. An outlet opening 108 in the lower housing shell 122 is in fluidic communication with an outlet chamber 106 inside the device 100. Both the inlet opening 104 and the outlet opening 108 may be cylindrical bores to which tubing or fluidic fittings may be attached. If the degassing device is integral with further components, for example, in the context of a cannula assembly as will be described below in more detail, the bores may not be present but may be replaced by fluid channels that are integral with housing components of the assembly.

It should further be noted that terms indicating a direction or geometrical relation, such as "upper" or "lower", generally refer to the corresponding drawings and are meant to aid the understanding, but do not imply any specific spatial orientation of the device during application.

Within the housing 120, 122, a hydrophilic membrane 110 as well as a hydrophobic membrane 112 are arranged side-by-side such that they form a planar and circular joined membrane 110, 112 with a hydrophilic section and a hydrophobic section.

Both membranes 110, 112 have circular peripheral edges 110*a*, 112*a* in their peripheral sections which smoothly fade into inner joint edges 110*b*, 112*b*. The joint edges 110*b*, 112*b* have the shape of a symmetric "S", with its point of symmetry being aligned with the center of the joined membrane. The joined membrane 110, 112 is arranged in a sandwich-like way between the housing shells 120, 122.

The lower housing shell 122 includes a joint rim 124 which has a top-view shape that corresponds to the joint edges 110*b*, 112*b*. Both membranes 110, 112 overlap the joint rim 124 in the area of the joint edges 110*b*, 112*b*. Both membranes 110, 112 are attached along their peripheral edges 110*a*, 112*a* to the housing shells 120, 122. Both membranes 110, 112 are further attached at their joint edges 110*b*, 112*b* to the joint rim 124. Attaching technologies such as ultrasonic welding, laser welding or adhesive bonding may be used for this purpose.

The joint rim 124 accordingly serves as a support structure for the membranes 110, 112. The membranes 110, 112 may contact each other along the joint 116, that is, the joint edges 110*b*, 112*b* may coincide. Alternatively, the membranes 110, 112 may be separated by a small gap which is bridged by the joint rim 124 and has a lateral dimension that is small as compared to its lengths.

As best seen from FIG. 2, the inlet chamber 102 extends over the whole area of the joined membrane 110, 112. The inlet chamber 102 is limited by a peripheral surface 102*a* which is defined by the upper housing shell 120 and is further limited by the joined membrane 110, 112. The peripheral surface 102*a* is parallel with the joined membrane 110, 112, resulting in the inlet chamber 102 being cylindrical as the joined membrane 110, 112. In this example, the inlet opening 104 is arranged over the hydrophobic membrane 112. It may, however alternatively be arranged at any different position of the inlet chamber 102, including its side walls.

The outlet chamber 106 is limited by a peripheral surface 106*a* which is defined by the lower housing shell 122 and is further limited by the joint rim 124 and the hydrophilic membrane 110. The peripheral surface 106*a* is parallel with the joined membrane 110, 112, such that the top-view of the outlet-chamber 106 corresponds to the top-view of the hydrophilic membrane 110.

A degassing opening 114 is arranged next to the outlet chamber 106 in a side-by-side arrangement. The degassing opening 114 is fluidically coupled with the inlet chamber 102 via the hydrophobic membrane 112. The degassing opening 114 is a cut-out in the lower housing shell 122. The shape of the cut-out corresponds to the planar view of the hydrophobic membrane 112. The degassing opening 114 is separated from the outlet chamber 106 via the joint rim 124. Via the degassing opening 114, the hydrophobic membrane 112 is fluidically coupled to the environment.

Thus in one embodiment, the operation of the degassing device 100, may be that the inlet chamber 102 includes a liquid-filled section and an air-filled section.

If the degassing device 100 is in a horizontal orientation with the gravity vector 210 being normal to the joined membrane 110, 112, the air will substantially form a cylinder within the inlet chamber 102. The top and bottom boundaries of the air cylinder are given by the peripheral surface 102*a* and by the joined membrane 110, 112. The air cylinder is surrounded by liquid.

Figure 4:
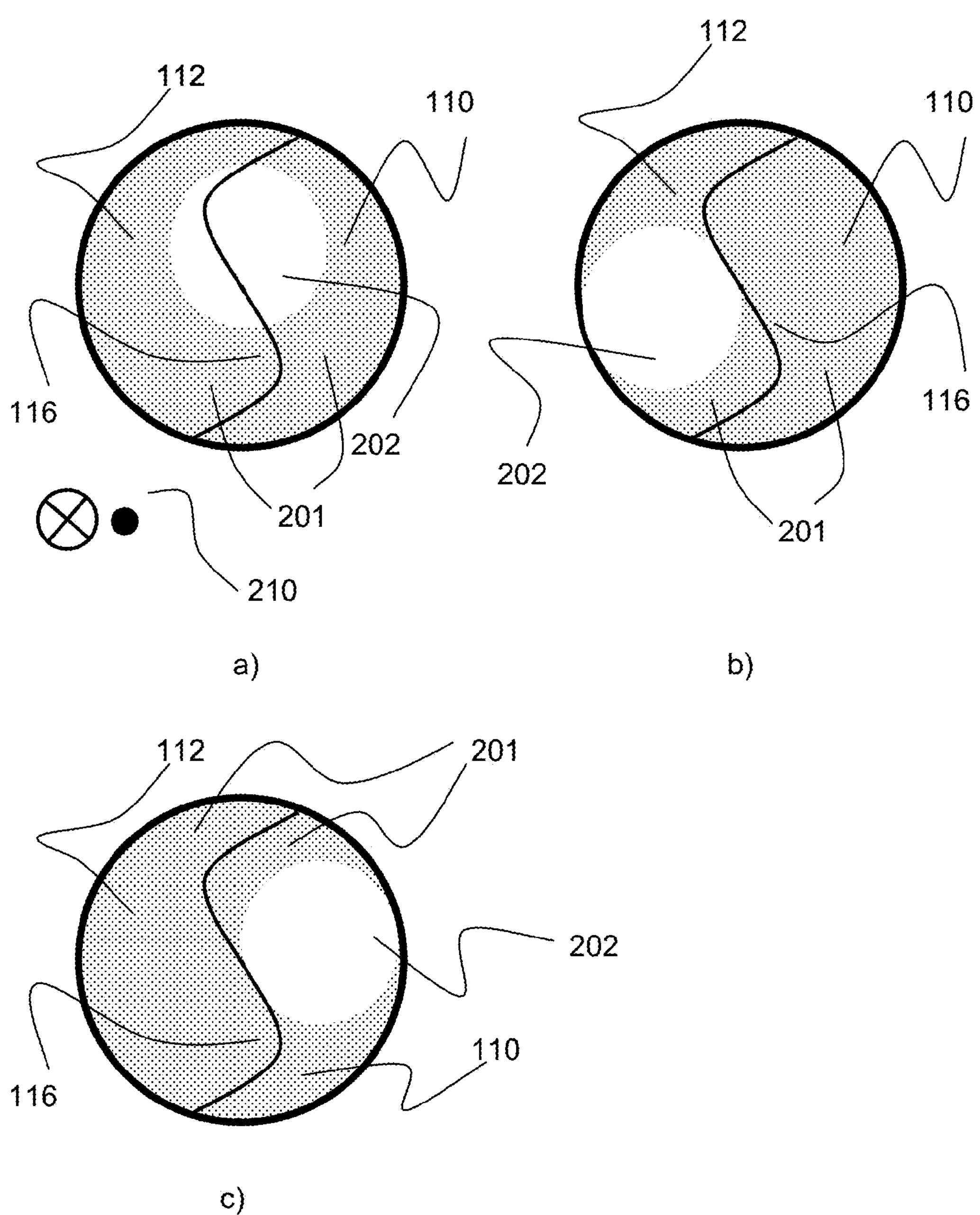
FIGS. 4*a*, 4*b* and 4*c* schematically show a top view of the inlet chamber of the degassing device of FIG. 1 in different situations.

FIG. 4 schematically shows a top view of the inlet chamber 102 with the upper housing shell 120 being cut-away for different situations. In all embodiments illustrated in FIGS. 4*a*-4*c*, the degassing device 100 may be horizontal with respect to gravity.

In the embodiment shown in FIG. 4*a*, the air cylinder 202 is located somewhere in the central region of the inlet chamber 102 and is in contact with both the hydrophilic membrane 110 and the hydrophobic membrane 112. The air cylinder 202 is surrounded by liquid 201. If further liquid and/or air is forced into the inlet chamber 102 via the inlet opening 104, air can leave the inlet chamber 102 via the hydrophobic membrane 112. Similarly, the liquid in the inlet chamber 102 contacts the hydrophilic membrane 110 and can accordingly exit the inlet chamber 102 and flow into the outlet chamber 106 via the hydrophilic membrane 110.

If the air cylinder 202 is completely located in the area of the hydrophobic membrane 112, as illustrated in FIG. 4*b*, the air can also exit the inlet chamber 102 via the hydrophobic membrane 112, even though some of its surface is blocked for the transfer of air by liquid. Liquid can exit the inlet chamber 102 via the hydrophilic membrane 110.

If the air cylinder 202 is completely located in the area of the hydrophilic membrane 110, as illustrated in FIG. 4*c*, it blocks some of its surface for the transfer of liquid to the outlet chamber 106. However, since the circumference of the air cylinder 202 is circular and the contour of the hydrophilic membrane 112 is non-circular, the air cylinder 202 will never cover the whole area of the hydrophilic membrane 110 and accordingly not block the transition of liquid into the outlet chamber 106.

Figure 5:
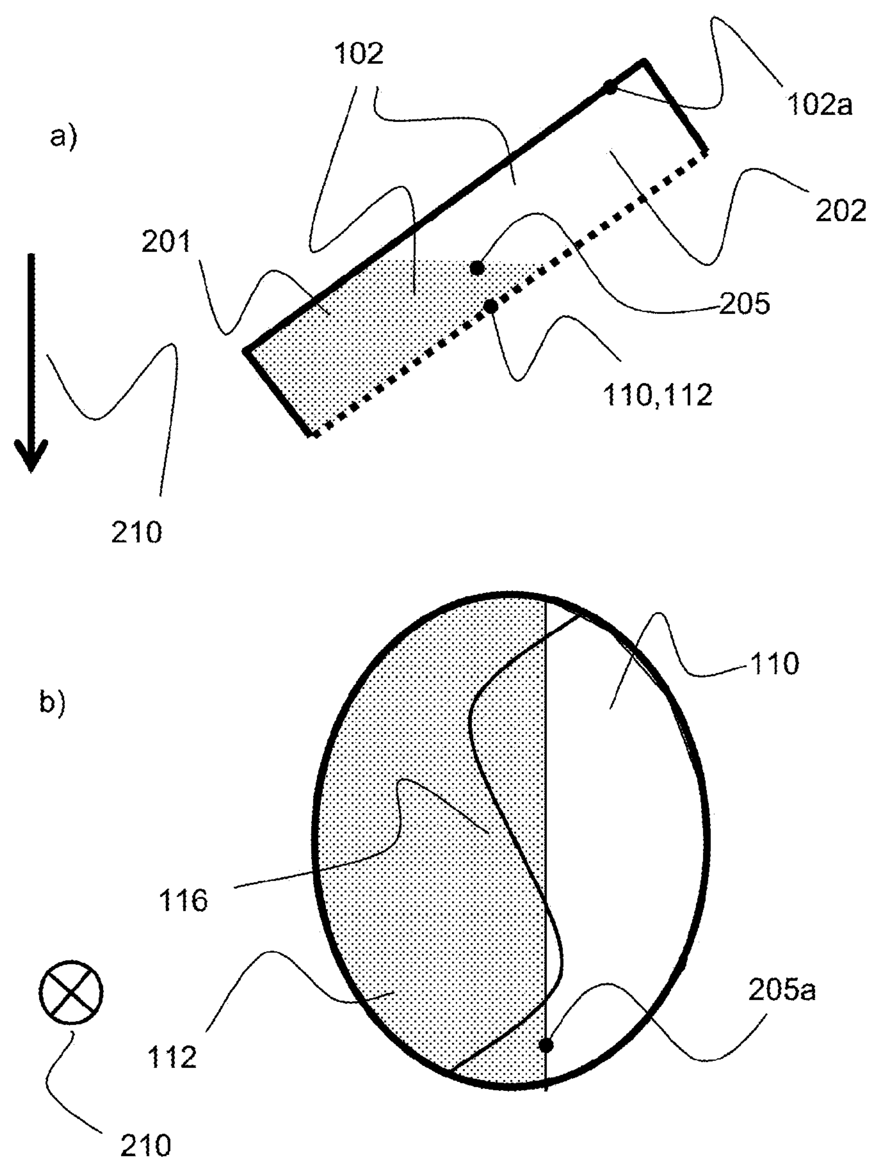
FIGS. 5*a* and 5*b* schematically show a sectional view of the inlet chamber of the degassing device of FIG. 1 in a further situation and a corresponding top view of the joined membrane.

FIG. 5*a* schematically shows a sectional view of the inlet chamber 102 if the degassing device is tilted into an orientation with the joined membrane 110, 112 not being normal to the vector of gravity 210. Here, the liquid-gas phase separation between the liquid-filled section 201 and the air-bubble, air cylinder 202 assumes the shape of a plane 205 extending between the peripheral surface 102*a* and the joined membrane 110, 112. Since the joint 116 is curved, it is always ensured that a liquid flow is enabled from the inlet 104 through the inlet chamber 102 and to the hydrophilic membrane 110. In an analogue way, a gas flow is always enabled to the hydrophobic membrane 112.

FIG. 5*b* shows a corresponding schematic view on the joined membrane 110, 112, indicating the line 205*a* of the liquid-gas phase separation on the joined membrane 110, 112. It can be seen that the liquid-gas phase separation 205*a* cannot coincidence with the joint 116 since the line 205*a* is substantially straight (neglecting surface effects) while the joint 116 is curved.

Figure 6:
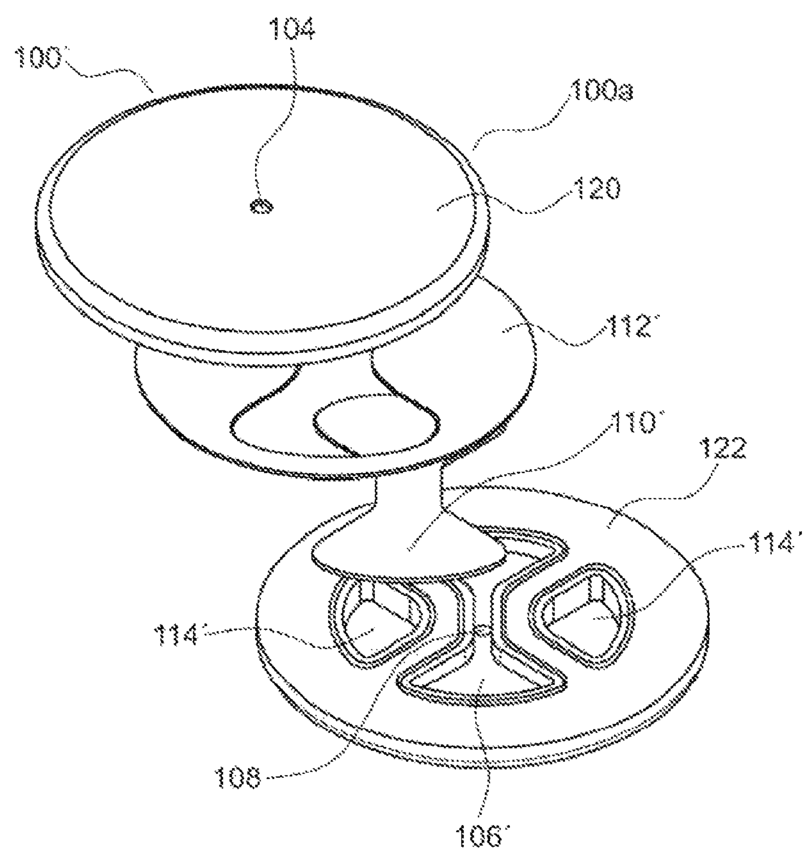
FIG. 6 shows a further embodiment of a degassing device in an exploded view.

FIG. 6 shows a further embodiment of the degassing device 100' in an exploded view. The overall design and the function of device 100' are similar to the previously discussed embodiments, such that the following description is focused on the differences.

In the degassing device 100', the hydrophilic membrane 110' is an embedded, correspondingly shaped cut-out in the hydrophobic membrane 112'. The arrangement results in the hydrophilic membrane 110' and the outlet chamber 106' having a hourglass-like form with a waistline. Active sections of the hydrophobic membrane 112' and corresponding degassing openings 114' are arranged on both sides of the waistline. The resulting joined membrane 110', 112' is circular like in the previously discussed embodiments of the degassing device 100. This is, however, not essential for either of the embodiments.

The joint (not referenced) between the hydrophilic membrane 110' and the hydrophobic membrane 112' corresponds to the shape of the hydrophilic membrane 110'. The inlet chamber of degassing device 100' (not visible FIG. 6) is, like in the degassing device 100, of cylindrical shape and is arranged between the joined membrane 110', 112' and the upper housing shell 120.

In the degassing device 110', the inlet opening 104 and the outlet opening 108 are arranged in the center of the circular housing shells 120, 122, resulting in the fluidic connections being coaxial with the degassing device 100'. The inlet opening 104 and the outlet opening 108 may alternatively be arranged at any different positions of the inlet chamber and the outlet chamber, respectively.

In a similar way as discussed above with reference to degassing device 100, the design of degassing device 100' and in particular of the joined membrane 110', 112' is such that liquid flow from the inlet opening 104 to the outlet opening 108 through the hydrophilic membrane 110' and from the inlet opening 104 to the degassing openings 114' through the hydrophobic membrane 112' is enabled for any orientation with respect to gravity as can be derived by geometrical considerations as previously discussed in similar embodiments of the degassing device 100.

Figure 14:
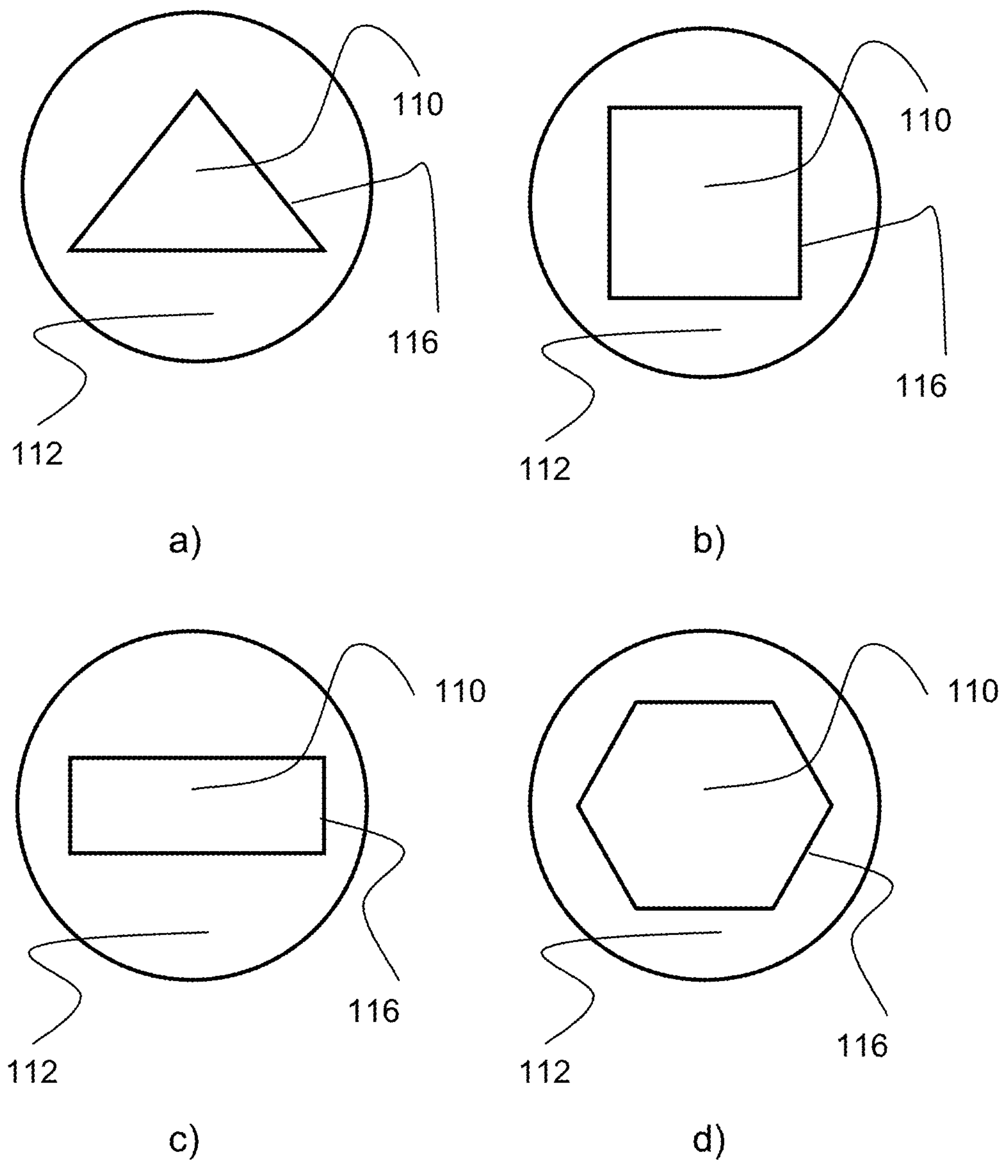
FIGS. 14*a*, 14*b*, 14*c* and 14*d* show a top view of the designs of a joined membrane.

FIGS. 14*a*-14*d* show further embodiments of the joined membrane 110, 112. For the designs illustrated in FIGS. 14*a*-14*d*, the hydrophilic membrane 110 is embedded into and surrounded by the hydrophobic membrane 112 and the joint 116 is a closed polygon. FIG. 14*a* shows a triangular joint 116, FIG. 14*b* shows a square joint 116, FIG. 14*c* shows a rectangular joint 116 and FIG. 14*d* shows a hexagonal joint 116. While the hydrophilic membrane 110 is shown as being centered with the hydrophobic membrane 112, this is not essential. Also, the arrangement of the hydrophilic membrane 110 and the hydrophobic membrane 112 may in principle be exchanged. Further possible shapes of the joint 116 may, for example, be an irregular closed polygon or a star.

Figure 7:
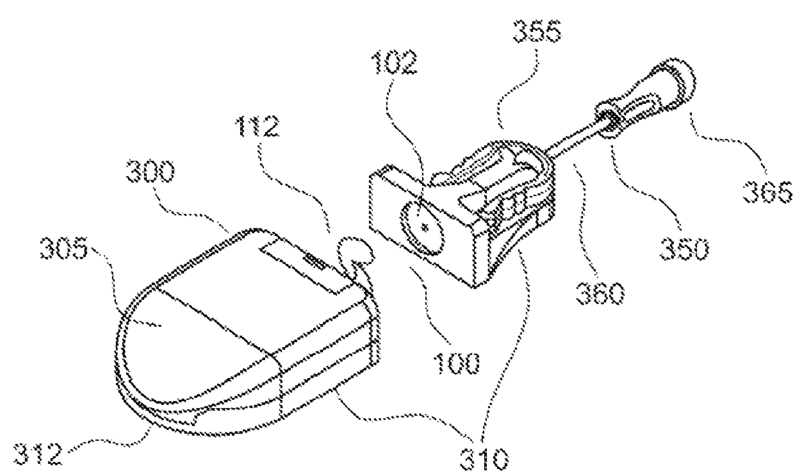
FIG. 7 shows an exploded view of a cannula assembly.
Figure 8:
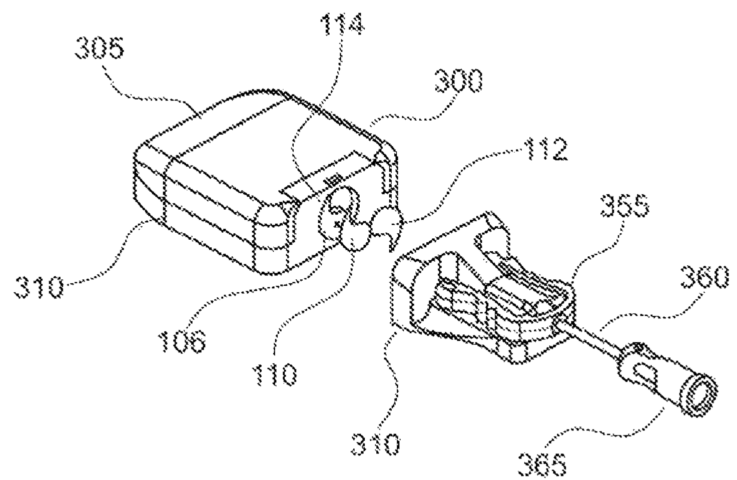
FIG. 8 show a further embodiment of a cannula assembly in an exploded view.

FIG. 7 and FIG. 8 show exploded views of a cannula assembly 300 with an attached tubing set 350. The cannula assembly includes a degassing device 100 as described in the above embodiments. The cannula assembly 300 is two-parted and includes a reusable portion 305 and a single-use or disposable portion 310. The single-use portion 310 includes a subcutaneous cannula 312 which may be made, for example, by medical grade stainless steel or a soft material, such as Teflon. The cannula 312 projects from a substantially flat underside of a housing (not referenced) of the single-use portion 310. The side of the housing from which the cannula 312 projects further includes an adhesive layer (not shown) by means of which the cannula assembly 300 can be secured to a person's skin for the application time of the disposable portion 310. While the cannula 312 projects substantially perpendicular from the housing in FIGS. 7 and 8, it may also include a smaller angle, of, for example, 30° with the housing. The application time is typically in the range of some days. The application time of the reusable portion 305 is typically in the range of several months or even years.

The single-use portion 310 is releasable coupled to the reusable portion 305 of the cannula assembly 300, for example, via a snap-fit connector.

The cannula assembly 300 includes a pressure sensor for fluidic pressure measurement directly upstream of the subcutaneous cannula 312. For this purpose, the single-use portion 310 includes a pressure measurement chamber with a pressure transfer membrane (both not visible). During operation, the pressure transfer membrane is deflected by the fluidic pressure of the liquid in the pressure measurement chamber. The reusable portion 305 includes an optical detector for determining the deflection of the pressure transfer membrane as well as corresponding evaluation and/or signal conditioning circuitry, like one or multiple filters, amplifiers, analogue-to-digital converters, or the like. The reusable portion 305 further comprises an energy supply for the pressure sensor, such as a rechargeable or non-rechargeable battery, and a typically wireless communication interface, such a Bluetooth RF interface, for communication with an infusion device.

The cannula assembly 300 can be releasably coupled with an ambulatory infusion device, such as an insulin pump, via tubing set 350. The tubing set 350 includes a cannula coupler 355 which engages, during operation, with a corresponding counterpart coupler (not referenced) of the cannula assembly 300, tubing 360 and an infusion device coupler 365 for releasably coupling to an infusion device. The length of the tubing 360 is typically in a range of about 30 centimeters to 1.5 meter. The fluidic connection is provided for transferring a drug from the infusion device to the subcutaneous cannula 312. Similar to the cannula assembly 300, the tubing set 350 is designed for a typical lifetime of some days. The exchange intervals of the cannula assembly 300 and tubing set 350 may be identical or different.

The single-use portion 310 further includes a degassing device 100 as described above. The single-use portion 310 is shown in the Figures as cut into two parts for illustrating the arrangement of the degassing device 100. The inlet opening of the degassing device 100 is fluidically coupled to the (not referenced) counter coupler that is designed for coupling to the cannula coupler 355. The outlet opening of the degassing device 100 is fluidically coupled to the pressure measurement chamber. In this way, gas and in particular air that is included in the drug stream is removed upstream of the pressure sensor.

Figure 9:
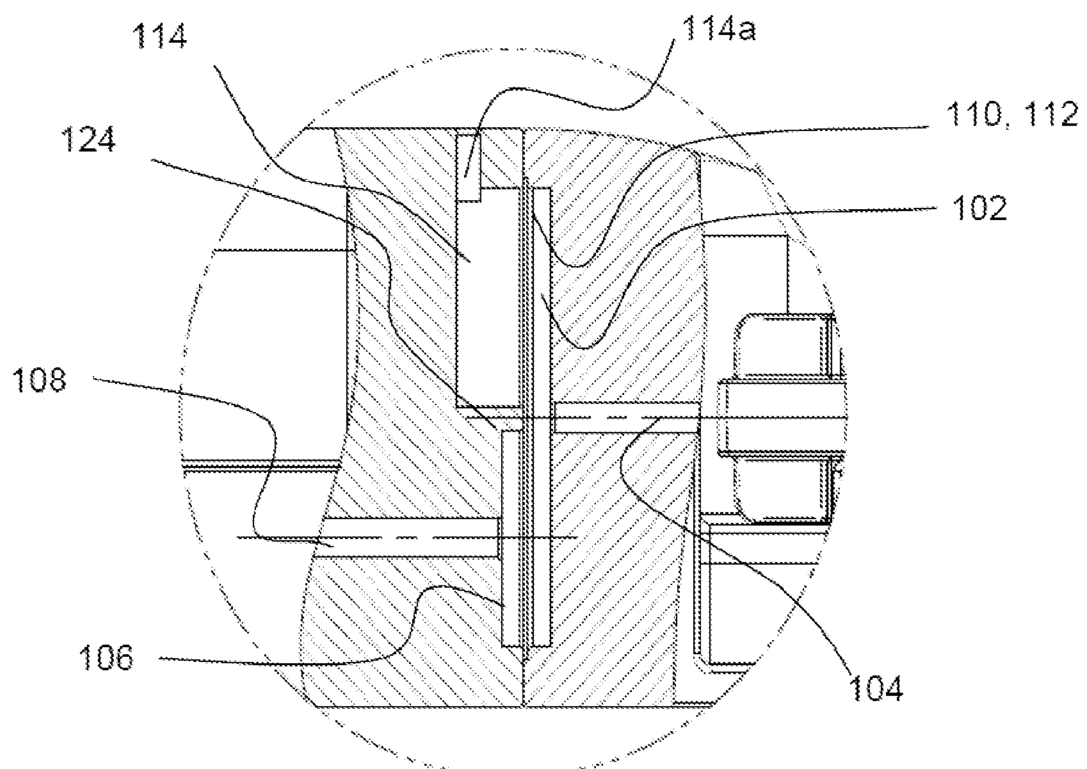
FIG. 9 shows a sectional view a degassing device included in the cannula assembly of FIGS. 7 and 8, respectively.

FIG. 9 shows the degassing device 100 of the cannula assembly 300 in a more detailed cross-sectional view. The degassing opening 114 is coupled with the environment via an aperture 114*a*. The aperture 114*a* has a sufficient cross section to allow gas to easily escape while being sufficiently small to protect the inside of the device, in particular the hydrophobic membrane 112, from mechanical damage and/or contamination. Alternatively, a greater portion or the total surface of the hydrophobic membrane 112 may be in direct contact with the environment.

The cannula assembly 300 and the tubing set 350 may be varied in a number of ways. For example, splitting the cannula assembly 300 into a reusable portion 305 and a single-use portion 310 is not required and an integral unit including all functional components may be used instead.

The cannula assembly 300 and the tubing set 350 may be designed in an integral way, thus avoiding the cannula coupler 355 of the tubing set 350 and the corresponding counter coupler. In dependence of the design of the infusion device, the tubing set 350 may further be omitted and the cannula assembly 300 may be directly coupled to the infusion device.

The pressure sensor may generally be of any design known in the art. For example, the deflection of the pressure transfer membrane may be determined capacitive, by strain gauges, or the like. Instead of connecting the cannula assembly 300 and the infusion device wirelessly, galvanic or optical coupling may be used. In this case, the tubing 350 includes electrical wires and/or optical fibers and the corresponding couplers include electrical and/or optical connectors.

The degassing unit 100 may be of any alternative design as discussed in the above embodiments.

Figure 10:
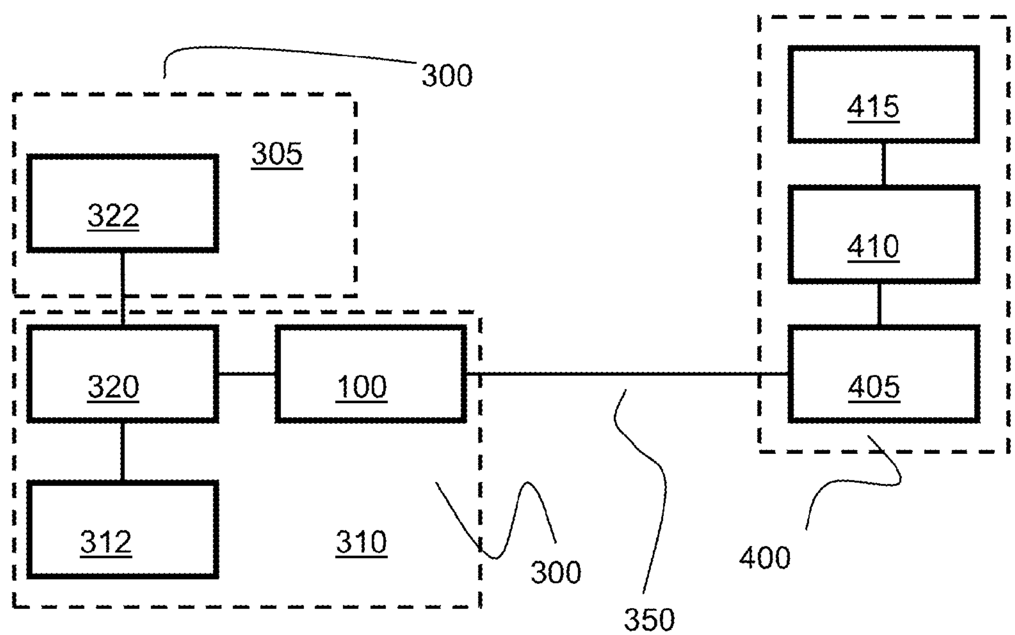
FIG. 10 shows a schematic view of an ambulatory infusion system.

FIG. 10 shows an ambulatory infusion system with cannula assembly 300 and tubing set 350 as described above and further an ambulatory infusion device 400 in a schematic structural view. The cannula assembly 300 may be designed as described above with reference to FIGS. 7 and 8, respectively. The pressure sensor includes a pressure measurement chamber 320 and an electronic unit 322. The electronic unit 322 includes an optical detector, further signal conditioning and analogue-to-digital conversion circuitry, an RF communication interface and a power supply as described above. The power supply is typically replaceable.

The infusion device 400 includes an electronically controlled dosing unit 410 and a corresponding electronic controller 415. The dosing unit 410 is operatively coupled with a drug container 405 which stores a liquid drug formulation to be infused. The drug container 405 has an outlet (not referenced) that is fluidically coupled with the tubing set 350. The dosing unit 410 may include a motor-driven spindle drive as known from typical state-of-the art ambulatory infusion devices. In this case, the drug container 405 is a cartridge with a plunger, the plunger being displaced via the spindle drive. The design of the dosing unit 410 and the drug container 405, however, is not essential. Alternative types of dosing units and/or drug containers may be used as well. For example, the drug container 405 may be flexible and pouch-like and may be fluidically coupled with a dosing unit that is arranged downstream of the drug container 405, the dosing unit 410 comprising a valve arrangement and a reciprocally and incrementally displaceable piston under control of the dosing unit 410. Such a dosing unit is disclosed in the WO 2008110263 A1. A further alternative pump design that may be used is a peristaltic pump.

The electronic controller 415 may be based on one or multiple microcontrollers and supplementary circuitry. During operation, the controller 415 controls the overall operation of the infusion device 400 and in particular the operation of the dosing unit 410. The controller 415 is further configured to process a pressure signal as provided from the pressure sensor 320, 322. The controller 415 is may be configured to detect a steep or a continuous pressure increase over time as typically occurs in the case of an occluded infusion cannula 312. The pressure sensor 320, 322 and the controller 415 may further be designed to detect a temporary pressure increase that is associated with each drug administration due to a fluidic resistance of cannula 312.

The infusion device 400 may further include components such as a power supply, e.g. a battery, a user interface, a communication interface for typically wireless communication with further devices such as a personal computer or a remote controller, and a tactile and/or an acoustical indicator. Those elements, however, are not essential in the present context. The circuitry of the infusion device 400 further includes a communication interface for receiving pressure measurement signals from the cannula assembly 300.

The infusion device 400 may be designed as a durable device with a usage time of typically some years, with the drug container 405 being disposable that is received in a corresponding compartment of the infusion device 400. Alternatively, further or all components of the infusion device 400 are disposable. The infusion device 400 may be a single device or may include modules that are designed for releasable coupling.

Figure 11:
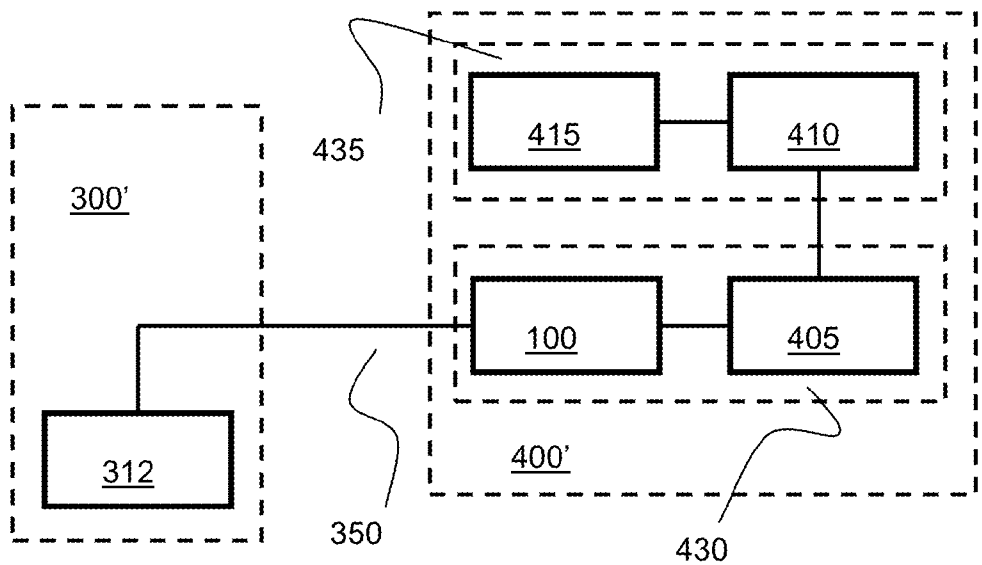
FIG. 11 shows a further embodiment of an ambulatory infusion system in a schematic view.

FIG. 11 shows a further embodiment of an ambulatory infusion system with an infusion device 400' and a cannula assembly 300' in a schematically structural view. In contrast to the previously described system, the degassing device 100 is arranged upstream of the tubing set 350. The degassing device 100 is provided integral with the drug container 405 as a single disposable unit. In this embodiment, a pressure sensor is not necessarily present and the degassing device 100 is mainly provided for the main or sole purpose of preventing air from entering the body.

The structural and functional features of the ambulatory infusion systems as described above may be varied and/or combined in various ways. For example, the pressure sensor 320, 322 and/or the degassing device 100 of the embodiment as illustrated in FIG. 10 may be part of the infusion device 400 rather than of the cannula assembly 300. In the embodiment illustrated in FIG. 11, the degassing device 100 may alternatively be included in the cannula assembly 300'. Furthermore, the degassing device 100 may be included by the tubing set 350 or be provided as a separate unit.

In all illustrated embodiments, the tubing set 350 does not need to be a separate unit but may be integral with either of the cannula assembly 300, 300' and/or the infusion device 400, 400', thus reducing the number of required couplers. The tubing set 350 may further be omitted. In those embodiments, the cannula assembly 300, 300' is directly coupled to the infusion device 400, 400', thus forming, during application, a single compact unit.

Besides or alternative to the pressure sensor 320, 322, the cannula assembly 300, 300' may further include alternative or additional functional components, such as an air bubble detector or a stimulating device for stimulating the body tissue in the area of the infusion cannula 312, as disclosed, e.g., in the WO 2007131567 A1.

In the embodiment according to FIG. 10, the communication between pressure sensor 320, 322 and the infusion device 400 may further be a wired communication with electrical cables and/or optical fibers which are included in the tubing set 350 and its connectors. In this case, a separate power supply may not be present in the cannula assembly 300.

Figure 12:
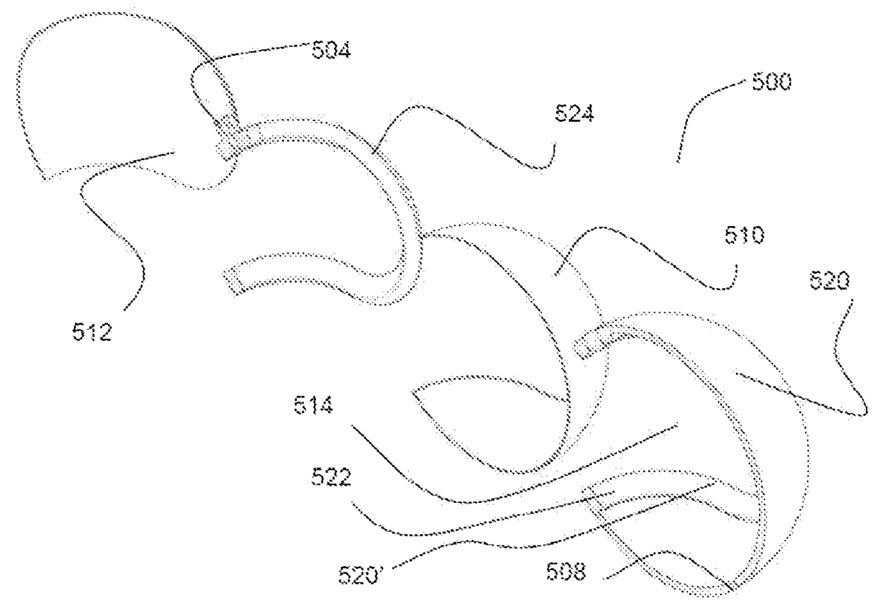
FIG. 12 shows a further embodiment of a degassing device in an exploded view.
Figure 13:
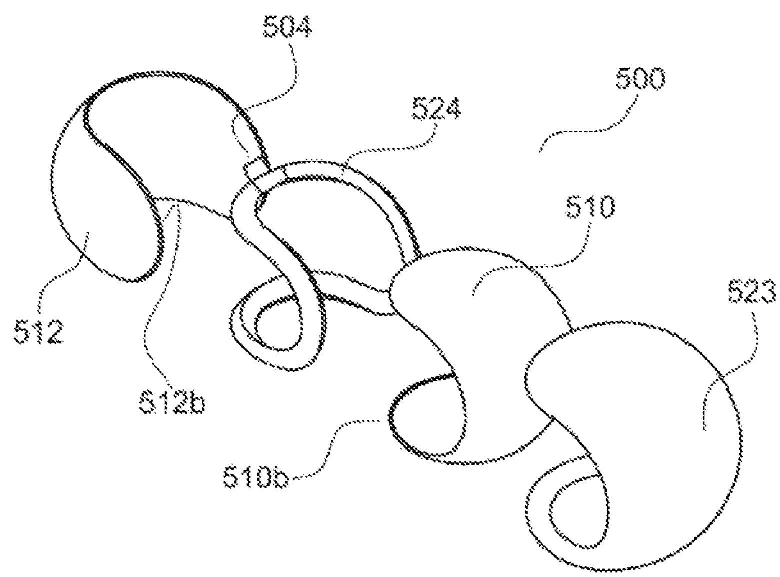
FIG. 13 show a further embodiment of a degassing device in an exploded view.

FIG. 12 and FIG. 13 show a further embodiment of a degassing device 500 in exploded views, with FIG. 12 being partly sectional. The degassing device 500 has an overall spherical 'ball-like' shape in the assembled state.

The hydrophilic membrane 510 and the hydrophobic membrane 512, or joined membrane 510, 512 with a hydrophilic section and a hydrophobic section having the shape of sphere sections, such that the joined membrane 510, 512 forms a complete sphere, with the inner volume of the sphere being the inlet chamber (not referenced). Both membranes 510, 512 are attached to a joint rim 524 along their joint edges 510*b*, 512*b*, respectively. The joint rim 524 has the geometry of a closed three-dimensional curve, thus defining the joint (not referenced). The inlet opening 504 is realized as a bore or the like in the joint rim 524.

The joint rim 524 with the joined membrane 510, 512 is attached to a housing shell 520. The housing shell 520 has the shape of a sphere section that substantially corresponds to the shape of the hydrophilic membrane 510. The housing shell 520 further has an edge 520' with a shape corresponding to the joint rim 524. Along the edge 520', the inner side of the housing shell 520 includes a circumferential rim 522. The joint rim 524 with the joined membrane 510, 512 smoothly fits into the opening 514 as defined by edge 520' and the circumferential rim 522. The joint rim 524 is attached to the housing shell 520 as described above. Due to the circumferential rim 522, a gap is present between the inner surface of the housing shell 520 and the hydrophilic membrane 510 such that the housing shell 520, the hydrophilic membrane 510 and the joint rim 524, in combination, define a volume serving as an outlet chamber (not referenced). The outlet opening 508 is realized by an aperture, for example, a bore, in the housing shell 520.

Because the housing shell 520 only extends over the hydrophilic membrane 510, the outside of the hydrophobic membrane 512 is in contact with the environment over its whole surface area. In this way, the opening 514 serves as degassing opening.

It should be noted that operation of the degassing device 500 neither depends on the spherical shape nor on a specific geometry of the joint edge. Instead of being spherical, the overall shape may, for example be an ellipsoid shape.

The geometry of the joint rim 524, and, thus, of the joint edge, may also be largely varied. A planar circular joint edge resulting in the hydrophilic membrane 510 and the hydrophobic membrane 512 being hemispheres, thus, a separation plane between a liquid-filled section and a gas-filled section of the inlet chamber may, in dependence of the relative amounts of liquid and gas in the inlet chamber as well as the orientation of the device, result in a blockage with the hydrophilic membrane being only in contact with gas and the hydrophobic membrane being only in contact with liquid.

What is claimed is:

1. A degassing device for removing gas bubbles from a liquid drug stream comprising:

an inlet chamber with an inlet opening, an outlet chamber with an outlet opening, and a degassing opening; and a hydrophilic membrane and a hydrophobic membrane, wherein the hydrophilic membrane fluidically couples the inlet chamber with the outlet chamber, enabling a transfer of liquid from the inlet chamber to the outlet chamber through the hydrophilic membrane, the hydrophobic membrane fluidically couples the inlet chamber with the degassing opening, enabling a transfer of gas from the inlet chamber to the degassing opening through the hydrophobic membrane, and, the hydrophilic membrane and the hydrophobic membrane being joined along a joint to establish a joined membrane, such that a line formed on the joined membrane by a liquid-gas phase separation of the gas bubbles and the liquid drug does not coincide with the joint independent of an orientation of the degassing device with respect to gravity.

2. The degassing device according to claim 1, wherein the joint is designed to be non-straight and non-circular.

3. The degassing device according to claim 2, wherein the joint is twofold bent.

4. The degassing device according to claim 1, wherein the hydrophilic membrane and the hydrophobic membrane are planar.

5. The degassing device according to claim 4, wherein the hydrophilic membrane and the hydrophobic membrane are co-planar.

6. The degassing device according to claim 1, wherein the joint comprises two end points, the two end points being on a periphery of the joined membrane.

7. The degassing device according to claim 1, wherein the joint takes the form of a closed curve.

8. The degassing device according to claim 1, wherein a peripheral surface of the inlet chamber is parallel to a peripheral surface of the outlet chamber, the peripheral surface of the inlet chamber facing the peripheral surface of the outlet chamber.

9. The degassing device according to claim 8, wherein the joined membrane is arranged between the peripheral surfaces of the inlet chamber and the outlet chamber, respectively.

10. The degassing device according to claim 1, further comprising a support structure, such that the support structure supports the joined membrane along the joint.

11. The degassing device according to claim 10, wherein the hydrophilic membrane and the hydrophobic membrane are permanently attached to the support structure.

12. The degassing device according to claim 1, wherein the degassing device is designed for a liquid flow in the range of 0.05 ml/min to 0.4 ml/min.

13. The degassing device according to claim 1, further including a liquid pressure sensor for measuring a liquid pressure downstream of the hydrophilic membrane.

14. An ambulatory infusion system comprising:

a drug container;

a cannula assembly including a subcutaneous cannula, the subcutaneous cannula being fluidically coupled to the drug container;

a degassing device comprising an inlet chamber with an inlet opening, an outlet chamber with an outlet opening, and a degassing opening, wherein the inlet opening of the degassing device is fluidically coupled to the drug container and the outlet opening of the degassing device is fluidically coupled to the subcutaneous cannula, and a hydrophilic membrane and a hydrophobic membrane, wherein the hydrophilic membrane fluidically couples the inlet chamber with the outlet chamber, enabling a transfer of liquid from the inlet chamber to the outlet chamber through the hydrophilic membrane, the hydrophobic membrane fluidically couples the inlet chamber with the degassing opening, enabling a transfer of gas from the inlet chamber to the degassing opening through the hydrophobic membrane, the hydrophilic membrane and the hydrophobic membrane being joined along a joint to establish a joined membrane, such that a line formed on the joined membrane by a liquid-gas phase separation of the gas bubbles and the liquid drug does not coincide with the joint independent of an orientation of the degassing device with respect to gravity; and a dosing unit, the dosing unit operatively coupled to the drug container.

15. The ambulatory infusion system according to claim 14, wherein the degassing device is integral with at least one of the cannula assembly or the drug container.

* * * * *